US007148380B2

(12) United States Patent
Wang et al.

(10) Patent No.: US 7,148,380 B2
(45) Date of Patent: Dec. 12, 2006

(54) BIO-ENERGY MUSCLE RELAXANTS

(75) Inventors: Chong Gang Wang, St. Laurent (CA); Yisheng Zhang, c/o Canaimex, 1630 Du College Street, St. Laurent, Quebec (CA) H4L 2M4; Pei Wang, c/o Canaimex, 1630 Du College Street, St. Laurent, Quebec (CA) H4L 2M4

(73) Assignees: Yisheng Zhang, Quebec (CA); ChingGang Wang, Quebec (CA); Pei Wang, Quebec (CA)

( * ) Notice: Subject to any disclaimer, the term of this patent is extended or adjusted under 35 U.S.C. 154(b) by 164 days.

(21) Appl. No.: 09/764,417

(22) Filed: Jan. 19, 2001

(65) Prior Publication Data

US 2002/0006962 A1    Jan. 17, 2002

Related U.S. Application Data

(60) Provisional application No. 60/180,795, filed on Feb. 7, 2000.

(51) Int. Cl.
*C07C 251/38* (2006.01)
*C07C 251/42* (2006.01)
*A61K 31/15* (2006.01)

(52) U.S. Cl. ..................................... 564/258; 514/640
(58) Field of Classification Search ................ 564/258; 514/640
See application file for complete search history.

(56) References Cited

U.S. PATENT DOCUMENTS 5,162,374 A * 11/1992 Mulieri et al. .............. 514/640

OTHER PUBLICATIONS

Database CAPLUS on STN, Acc. No. 1989:205508, Higuchi et al., 'Butanedione monoxime suppresses contraction and ATPase activity of rabbit skeletal muscle.' J. Biochem. (Tokyo) (1989), 105(4), pp. 638-643 (abstract).*
Database CAPLUS on STN, Acc. No. 1976:130141, Bernadou et al., Eur. J. Med. Chem.—Chim. Ther. (1975), 10(6), p. 599-601 (abstract).*
Database CAPLUS on STN, Acc. No. 1994:475379, Sellin et al., Pharmacology & Toxicology (Oxford, UK), (1994), 74(6), p. 305-13 (abstract).*
Database CAPLUS on STN, Acc. No. 1960:80476, Ferris, A. F., J. Organic Chemistry (1960), 25 p. 12-18 (abstract).*
Database CAPLUS on STN, Acc. No. 1964:483758, GB 966849 (Aug. 19, 1964) (abstract).*
Database CALUS on STN, Acc. No. 1973:442422, Matyushin et al., Izvestiya Akademii Nauk SSSR, Seriya Khimicheskaya (1973), 4, p. 842-6 (abstract).*
Database CAPLUS on STN, Acc. No. 1975:277798, Bernadou et al., Comptes Rendus des Seances de I'Academie des Sciences, Serie D: Sciences Naturelles (1974), 278(26), p. 3391-3 (abstract).*
Database CAPLUS on STN, Acc. No. 1975:609837, Burkin et al., J. of Inorganic and Nuclear Chemistry (1975), 37(10), p. 2187-95 (abstract).*
Database CAPLUS on STN, Acc. No. 1976:180019, Winter et al., US 39321246 (Jan. 6, 1976) (abstract).*
Database CAPLUS on STN, Acc. No. 1980:110465, Lehr et al., Helvetic Chimica Acta (1979), 62(7), p. 2258-75 (abstract).*
Database CAPLUS on STN, Acc. No. 1980:502007, Preston, J. S., J. of Inorganic and Nuclear Chemistry (1980), 42(3), p. 441-7 (abstract).*
Database CAPLUS on STN, Acc. No. 1986:496171, Rizzi et al., Food Chemistry (1986), 20(3), p. 165-74 (abstract).*
Database CAPLUS on STN. Acc. No. 1992:425702, Adams et al, by J. of the Chemical Society, Perkin Transactions 2: Physical Organic Chemistry (1972-1999)(1991), 11, p. 1809-18 (abstract).*
Pharmacology & Toxicology (1994), 74(6), p. 305-313.*

* cited by examiner

*Primary Examiner*—Brian Davis
(74) *Attorney, Agent, or Firm*—Merchant & Gould P.C.

(57) ABSTRACT

Human muscle tissues involve striated and smooth muscles. Each muscle tissue possesses its own special function. Differences of physiology functions among the muscle tissues are mainly determined by their various initiation and signal transmission systems, defined as the pre-muscle molecular motor mechanism, or initiating and regulating mechanism. The current medications, drugs, and therapies for diseases and symptoms related abnormal increased muscle tone or excessive muscle contraction are aimed just at the pre-muscle molecular motor mechanisms, whereas without directly intending to effect on the muscle molecular motor mechanism i.e. the contractile apparatus mechanism at all, which, however, is in common for all kinds of muscle tissues. The muscle molecular motor mechanism mainly involves recycling of actin-myosin filament cross-bridge formation and sliding movement. In the process, bio-energy provided by ATP hydrolysis is necessarily required. Therefore, abnormal increased muscle tone or excessive contraction of muscle tissues under diseased conditions may be modified by inhibition of the muscle molecular motor with the actin-myosin ATPase inhibitor, which blocks hydrolysis of ATP, then reduces release of bio-energy for the muscle contraction.

Our studies in vitro and in vivo have demonstrated that BDM, an ATPase inhibitor, thereby, its analogues, derivatives, and other chemicals possessing similar effect on ATPase may be used as bio-energy muscle relaxants (general muscle relaxants).

9 Claims, No Drawings

BIO-ENERGY MUSCLE RELAXANTS

CROSS-REFERENCE TO RELATED APPLICATIONS

This application claims priority under 35 USC §119(e) of U.S. application Ser. 60/180,795 filed Feb. 7, 2000, now abandoned.

TECHNICAL FIELD

The present invention relates to a muscle relaxant and to method of treating muscle contraction-related diseases.

BACKGROUND OF THE INVENTION

Human Muscle Tissues

By the end of $2^{nd}$ or $3^{rd}$ week of embryonic development, some cells of the ectoderm proliferate inward to become primitive streak. Then the cells of primitive streak start to rapidly grow and form mesoderm, from which three main group of human muscle tissues (skeletal muscle, cardiac muscle and smooth muscle) are gradually differentiated and shaped up during the following months.

Skeletal Muscle

Skeletal muscle consists of muscle fibers, i.e. bundles of 1 to 40 mm long, cylindrical and multinucleated muscle cells with a diameter of 10 to 100 μm. Oval nuclei are usually found under the membrane of the muscle cells. Skeletal muscles are mainly attached to skeletal bones to carry out rapid and forceful but discontinuous voluntary contraction for various movements of the body, although some contractions are also seen in viscera, such as diaphragm. As observed with light microscope, longitudinally sectioned muscle cells or fibers show cross-striations of alternating light and dark bands. The darker bands are called A bands with width of 1.5 μm, which are anisotropic, i.e. birefringent in polarized light, at mid A band, there is a less dark area, i.e. H band, which is bisected by a darker middle line, i.e. M line. The lighter bands, called I bands, 0.8 to 1.5 μm in width, are isotropic, i.e. they do not alter polarized light. Each I band is bisected by a dark transverse line, the Z line.

The smallest repetitive functional subunit of the contractile apparatus is called sarcomere, which extends from Z line to Z line, and about 2~3 μm long in resting muscle. The sarcoplasm is filled with long cylindrical filamentous bundles called myofibrils, which have a diameter of 1~2 μm and run parallel to the long axis of the muscle fiber, consisting of an end-to-end chain-like arrangement of sarcomeres. Laterally, it exhibits a characteristic pattern of transverse striations. This sarcomere pattern is mainly due to the presence of two types of filaments, thick and thin, that are lying parallel to the long axis of the myofibrils in a symmetric pattern. The thick filaments are 1.6 μm long and 15 nm wide, occupying the A band, i.e. the central portion of the sarcomere. The thin filaments, which are 1.0 μm long and 8 nm wide, run between and parallel to the thick filaments and have one end attached to Z line. As a result of this arrangement, the I bands consist of the portion of the thin filaments that do not overlap the thick filaments. The A bands are composed mainly of thick filaments in addition to portions of overlapping thin filaments. H bands are less dark zones in the center of band A, which corresponds to a region consisting only of the rod-like portion of the myosin molecules. Bisecting the H band is the M line, i.e. a region where lateral connections are made between adjacent thick filaments. The major protein of the M line is creatine kinase, which catalyzes the transfer of a phosphate group from phosphocreatine to ADP necessary for the production of ATP, thus providing the supply of ATP necessary for muscle contraction.

Striated muscle filaments contain four main proteins: actin, tropomyosin, troponin and myosin. Thin filaments are composed of the first three proteins, whereas thick filaments consist primarily of myosin.

Cardiac Muscle (Myocardium)

One special striated muscle, muscle cells are about 15 μm in diameter and 80~100 μm in length, each cardiac muscle cell possesses only one or two centrally located pale-staining nuclei and distributed only in the heart, cross striations may be seen under light microscope. During embryonic development, cardiac muscle cells form complex junctions between their extended processes, making cells within a chain often bifurcate, or branch, and bind to cells in adjacent chains. In addition, a unique distinguishing character of cardiac muscle is presence of dark-staining transverse lines that cross the chains of cardiac cells at irregular intervals, named intercalated disks. These disks represent junctional complexes found at the interface between adjacent cardiac muscle cells, so as to prevent cells from pulling apart under constant contractile activities and provide ionic continuity between adjacent cells, allowing the signal to contract to pass in a wave from cell to cell. Consequently, heart consists of tightly knit bundles of cells, interwoven in a fashion that provides for a characteristic wave of contraction that leads to a wringing out of the heart ventricles. It can perform continuous, quick and strong contraction, functioning as a center pump of circulation system, which is not controlled by will, but which belongs to non-voluntary muscle.

The structure and function of the contraction proteins in cardiac cells are virtually the same as in skeletal muscle. The T-tubule system and sarcoplasmic reticulum, however, are not as regularly arranged in the cardiac myocytes. The T tubules are more numerous and larger, but sarcoplasmic reticulum is not as well developed in ventricular muscle than in skeletal muscle. Cardiac muscle cells contain numerous mitochondria, which occupy 40% or more of the cytoplasmic volume, reflecting the need for continuous aerobic metabolism in heart muscle. By comparison, only about 2% of skeletal muscle fibers are occupied by mitochondria. Fatty acids, transported to cardiac muscle cells by lipoproteins, are the major fuel of the heart.

Smooth Muscle

Smooth muscle is composed of elongated fusiform non-striated cells, ranging in size from 20 μm to 500 μm, each cell has a single nucleus located in the center of the broadest part of the cell. Each of the cells is enclosed by a basal lamina and a network of reticular fibers, which serve to combine the force generated by each smooth muscle fiber into a concerted action, e.g. peristalsis in the intestine. A rudimentary sarcoplasmic reticulum is present, similar to that of striated muscle, but find no T tubules in smooth muscle cells. They are major constituents in the walls of hollow visceral organs, such as bronchial tree, alimentary canal, biliary tract, urinary tract, vasculatures, uterus, and so on. It may perform slow and sustained contraction, carrying out their functions respectively. Smooth muscle also belongs to non-voluntary muscle.

The characteristic contractile activity of smooth muscle is related to the structure and organization of its actin and myosin filaments, which do not exhibit the paracrystalline organization present in striated muscles. In smooth muscle cells, bundles of myofilaments crisscross obliquely through the cell, forming a lattice-like network. These bundles consist of thin filaments (5 to 7 nm) containing actin and tropomyosin, and thick filaments (12 to 16 nm) containing myosin. Both structural and biochemical studies reveal that smooth muscle actin and myosin contract by a sliding filament mechanism similar to that occurring in striated muscles.

An influx of $Ca^{2+}$ is involved in the initiation of contraction in smooth muscle. $Ca^{2+}$, however, interacts with actin only when the myosin light chain is phosphorylated. For this reason, and because the tropomyosin complex of skeletal muscle is absent, the contraction mechanism of smooth muscle differs somewhat from skeletal and cardiac muscle. $Ca^{2+}$ binds with calmodulin, a calcium-binding protein, to form $Ca^{2+}$-calmodulin complex. The $Ca^{2+}$-calmodulin complex activates myosin light chain kinase, the enzyme responsible for the phosphorylation of myosin light chain. Contraction or relaxation of smooth muscle may be regulated by hormones via cyclic AMP (cAMP). When a level of cAMP increases, myosin light-chain kinase is activated, myosin light chain is phosphorylated, and the cell contracts. A decrease in cAMP has the opposite effect, reducing contractibility.

Smooth muscle cells have an elaborate array of 10 nm intermediate filaments, coursing through their cytoplasm. Desmin (skeletin) has been identified as the major protein of intermediate filaments in all smooth muscles, and vimentin is an additional component in vascular smooth muscle. Two types of dense bodies appear in smooth muscle cells. One is membrane associated, the other is cytoplasmic. Both contain α-actinin and are thus similar to the Z lines of striated muscles. Both thin and intermediate filaments insert into dense bodies that transmit contractile force to adjacent smooth muscle cells and their surrounding network of reticular fibers.

Smooth muscle usually has spontaneous activity in the absence of nervous stimuli. Nervous stimuli have thus the function of modifying activity of the smooth muscle rather than, as in skeletal muscle, initiating it.

Mechanisms of Muscle Contraction

Skeletal Muscle Contraction

Skeletal muscle contraction involves the following processes:

a) a neuro-impulse for a movement starts from the central nervous system. The neuro-impulse is then transmitted along motor nerve fibers (axons) and reaches the motor end-plate (myoneural junction);

b) a neurotransmitter, acetylcholine, is released from the axon terminals;

c) the released acetylcholine binds to acetylcholine receptors in the sarcolemma at the junctional folds;

d) binding of the neurotransmitter makes the sarcolemma more permeable to sodium, resulting in membrane depolarization at the motor end-plate;

e) the depolarization is propagated along the surface of the muscle cells and deep into the muscle fibers via the triad, T tubule system; and f) the depolarization signal is passed to the sarcoplasmic reticulum (SR), and induces $Ca^{2+}$ release from SR cistern, which initiates the contraction cycle as the following mechanisms:

(i) high concentration $Ca^{2+}$ ions ($10^{-5}$ M) within the sarcoplasmic reticulum cistern are passively released into the vicinity of the overlapping thick and thin 2+filaments, increasing the Ca ion concentration locally ($10^{-6}$ to $10^{-7}$ M);

(ii) the $Ca^{2+}$ ions bind to TnC subunit of troponin, the signal is immediately transmitted to tropomyosin by TnI subunit, and induces myosin-ATP to be converted into an active complex;

(iii) the spatial configuration of the three troponin subunits changes and drives the tropomyosin molecule deeper into the groove of the actin helix, so as to expose the myosin-binding site on the actin components, making actin free to interact with the head of the myosin molecule;

(iv) the head of myosin molecule interacts with actin at the binding site, resulting in formation of actin-myosin cross-bridge. The actin-myosin ATPase is activated, degrading ATP into ADP and Pi with a release of bio-energy, required for movement of muscle molecular motor—a deformation, or bending, of the head and a part of the rod-like portion of the myosin;

(v) The movement of the myosin head pulls the actin filaments (thin filaments) to slide over the myosin filaments (thick filaments), drawing the thin filaments further into the A band; and (vi) The actin-myosin cross-bridge binds a new ATP molecule causing detachment of the bridge, resetting the myosin head reset for another contraction cycle (If no ATP available, the actin-myosin bridge becomes stable, accounting for the extreme muscular rigidity that occurs after death).

Although a large number of myosin heads extend from the thick filaments, at any one time during the contraction, only a small number of heads align with available actin-binding sites. As the bound myosin heads move the actin, the movement provides for more actin-binding sites available for alignment of new actin-myosin bridges. A single muscle contraction is the result of hundreds of cycles of actin-myosin cross-bridge-forming, sliding, and bridge breaking. The contraction activity that leads to a complete overlap between thin and thick filaments continues until $Ca^{2+}$ ions are removed and the troponin-tropomyosin complex again covers the myosin binding site at actin molecule. During contraction, the I band decreases in size as thin filaments penetrate into the A band. The H band—the part of the A band with only thick filaments—diminishes in width as the thin filaments completely overlap the thick filaments. A net result is that each sarcomere, and consequently the whole muscle cell, is greatly shortened, although there is no change in length of both thin and thick filaments themselves.

Cardiac Muscle Contraction

The rhythmic cardiac muscle contraction is initiated by self-generated rhythmic impulses, which normally starts from nodus sinuatrialis, then is transmitted along atrial muscle fibers and cardiac conductive system, which consists of nodus atrioventricularis, fasciculus atrioventricularis (His fasciculus), crus sinistrum, crus dextrum and Purkinje fibers, finally reaches to ventricular muscle fibers. Meanwhile, the impulse sequentially results in depolarization of atrial cardiac muscle, then ventricular cardiac muscle. The events following the depolarization to cause cardiac muscle contraction are similar to those occurring in skeletal muscle, i.e. $Ca^{2+}$ release, recycling of actin-myosin filament cross-bridge formation, and sliding movement.

In addition, there is rich autonomic nerve supply to cardiac muscles, so that both sympathetic and parasympathetic nervous impulses may apparently modify activities of cardiac muscle contraction.

Smooth Muscle Contraction

Smooth muscles are non-voluntary muscles. They may spontaneously contract but the contraction is slow and sustained. Many factors, such as mechanical stimuli, physical factors, chemicals, hormones, neurotransmitters and so on, may substantially influence smooth muscle contraction. Generally smooth muscle contraction occurs as follows:
 a) an initial factor firstly causes $Ca^{2+}$ influx into smooth muscle cells, or induces intra-cellular $Ca^{2+}$ release from sarcoplasmic reticula (SR);
 b) The $Ca^{2+}$ combines with a calcium binding protein, such as calmodulin, to form $Ca^{2+}$-protein ($Ca^{2+}$-calmodulin) complex;
 c) The $Ca^{2+}$-protein complex activates myosin light chain kinase (MLCK);
 d) The myosin light chain kinase (MLCK) catalyzes phosphorylation of myosin light chain (MLC);
 e) The phosphorylated myosin light chain activates actin-myosin ATPase; and
 f) The activated actin-myosin ATPase catalyzes hydrolysis of ATP, resulting in release of bio-energy for smooth muscle contraction.

The subsequent events, i.e. the mechanism of smooth muscle actin-myosin interaction, recycling of actin-myosin cross-bridge formation, thin and thick filament sliding, are similar to those occurring in a skeletal muscle contraction.

It would be highly desirable to be provided with a new muscle relaxant for smooth and cardiac muscles.

SUMMARY OF THE INVENTION

One aim of the present invention is to provide a new muscle relaxant for smooth and cardiac muscles.

Another aim of the present invention is to provide new uses and method of use of this new muscle relaxant of the present invention.

In accordance with the present invention there is provided a muscle relaxant as defined in formula I:

$$R_1C(=NOH)COR_2 \qquad (I)$$

Wherein $R_1$ and $R_2$, identical or different, are independently selected from the group consisting of $C_{1-8}$ linear or branched alkyl, such as methyl, ethyl, and propyl, and a cycloalkyl, with the proviso that $R_1$ and $R_2$ are not both methyl group, said muscle relaxant inhibiting actin-myosin ATPase of smooth, cardiac and striated muscle.

In accordance with the present invention, there is also provided a pharmaceutical composition comprising the muscle relaxant described herein and a pharmaceutically acceptable excipient. The pharmaceutical composition may be formulated with a pharmacologically acceptable carrier vehicle in an aerosol, a lotion, a tablet, a capsule, or an injection. It may be administered by inhalation, orally, topically, parentally, on mucous or skin tissues, subcutaneously, intramuscularly, intravenously, intraperitoneally or topical tissue infiltration injections.

Still in accordance with the present invention, there is provided a method for treating and/or preventing a striated muscle contraction-related disease, said method comprising the step of administering the muscle relaxant described herein to a patient in need thereof. The muscle contraction-related disease may be for example selected from the group consisting of a spasm of skeletal muscle, epilepsy, Parkinson's disease, painful spasm, fatigue spasm, and muscle spasm caused by pathogenesis, tetanus, infectious diseases, neurological diseases, and toxic spasm.

Further in accordance with the present invention, there is also provided a method for treating and/or preventing a smooth or cardiac muscle contraction-related disease, said method comprising the step of administering to a patient in need thereof a muscle relaxant as defined in formula II:

$$R_1C(=NOH)COR_2 \qquad (II)$$

Wherein $R_1$ and $R_2$, identical or different, are each selected from the group consisting of $C_{1-8}$ linear or branched alkyl, and cycloalkyl, said muscle relaxant inhibiting actin-myosin ATPase of smooth and cardiac muscle. The muscle contraction-related disease may be for example selected from the group consisting of asthma, spasm or trachea-bronchial tree smooth muscle, diaphragm muscle abnormal contraction, breathlessness, dyspnea, diaphragmatic convulsion, hypertension, abnormal contraction of bronchial smooth muscle, abnormal and/or excessive contraction of smooth muscle in gastro-intestinal tract, biliary, pancreatic and tracts, spasm of vascular smooth muscle in systemic, coronary and pulmonary circulation, and microcirculatory smooth muscle, systemic hypertension, malignant hypertension, hypertension crisis, symptomatic hypertension, pulmonary hypertension, pulmonary infarction, angina pectoris, infarction, cardiac infarction, and microcirculation malfunction under shock condition.

Physiological functions of the muscle tissues are various, and differences among them are mainly determined by the initiating and regulating mechanism for each kind of special muscle tissue. All muscle tissues, however, possess a common similar property of contraction as a contractile apparatus, i.e. the muscle molecular motor, for which the mechanism basically is the same (recycling of actin-myosin filament cross-bridge formation and sliding movement). The process requires bio-energy provided by ATP hydrolysis, which relies on actin-myosin ATPase activity. Therefore, by inhibition of muscle molecular motor with the ATPase inhibitor(s), i.e. bio-energy muscle relaxant(s), abnormal increased muscle tone or excessive contraction of any kind of muscle tissues may be modified, so as to relieve the related diseases or symptoms.

DETAILED DESCRIPTION OF THE PREFERRED EMBODIMENT

Human muscle tissues originate from the embryonic mesoderm, that is then gradually differentiated into mainly three group of muscle tissues as skeletal muscle, cardiac muscle (myocardium), and smooth muscle along with the later individual embryonic developing process.

Each kind of muscle tissue has its own mechanism to cause contraction under normal or pathophysiological conditions, which, besides muscle-molecular motor, may be regarded as its own special initiation and signal transmission system, i.e. the initiating and regulating mechanism, so as to maintain various physiological activities and reactions under pathological situations of human body. At a molecular level, however, a final completion of a muscle contraction relies on the mechanism of the muscle contractile apparatus, i.e. muscle molecular motor mechanism (recycling of the actin-myosin filament cross-bridge formation and sliding movement). In this sense, therefore, all kinds of muscle tissues possess a common property for their basic physiologic contraction function.

Bio-energetically, running the muscle molecular motor requires bio-energy released from ATP hydrolysis, which is catalyzed by actin-myosin ATPase. Therefore, if the ATPase is inhibited, no ATP would be produced and thus available to be hydrolyzed, depriving the muscle molecular motor of bio-energy, preventing muscle contraction.

In this way, an abnormal increased muscle tone or excessive muscle contraction under pathophysiological situations, no matter what kind of muscle tissues, may be modified by using the actin-myosin ATPase inhibitor(s). The actin-myosin ATPase inhibitors, therefore, may be regarded as bio-energy muscle relaxants (or named generally muscle relaxants).

Common Property in Muscle Contraction

Muscle Molecular Motor Mechanism

Although there are many differences in the mechanisms of physiological functions among the various muscle tissues before muscle molecular motor action, the common property of recycling of actin-myosin filament cross-bridge formation and sliding movement is still present in all kinds of muscle contractile processes. Bio-energetically, during muscle contraction, no matter what kind of muscles, or how does the mechanism operate before muscle molecular motor, all muscle contractions are basically the same at the muscle molecular motor level. First there is activation of actin-myosin ATPase. Then there is hydrolysis of ATP at myosin head area, causing a release of bio-energy, necessary for the contractile apparatus—muscle molecular motor—to carry out recycling of actin-myosin filaments cross-bridge and sliding movement.

The mechanism involved in these steps may be defined as "muscle molecular motor mechanism", i.e. contractile apparatus mechanism. This is a common mechanism for all kinds of muscle tissues of human and animals.

Generally, therefore, mechanisms involved in any kind of muscle contractions, in fact, may be divided into two aspects: one aspect is the initiating and regulating mechanism, which involves all events related to muscle contraction happening before the muscle molecular motor action, so that it may also be called as pre-muscle molecular motor mechanism. The second aspect is the muscle molecular motor mechanism, i.e. contractile apparatus mechanism mentioned above. Although each kind of muscle has its own pre-muscle molecular motor mechanism for its contraction, the molecular motor mechanism basically is the same in all kinds of muscle tissues.

Current medications, drugs, and therapies for those diseases or symptoms related to abnormal increased muscle tone or muscle contraction mainly are aimed just at the pre-muscle molecular motor mechanism, i.e. the initiating and regulating mechanism, whereas without directly intending to effect on the muscle molecular motor mechanism. Examples of abnormal increased muscle tone or excessive contraction of smooth muscle are given hereinafter.

Asthma

In the treatment of asthma, various drugs, such as $P_2$-agonists, glucocorticoids, methylxanthines, non-steroidal anti-inflammatory agents, leukotriene synthesis inhibitors, leukotriene receptor antagonists, lipoxygenase inhibitors, and agents designed to inhibit the effects of cytokines, including reducing production of the cytokines and/or antagonists against the cytokines that up-regulate allergic inflammation such as IL-1, IL-4, IL-5, and IL-13 etc., and regulating of IgE synthesis, anti-IgE antibody, cytokines that down-regulate allergic inflammation, target the pre-muscle molecular motor mechanism.

Hypertension

In the treatment of hypertension, the current drugs and therapies include vasodilators such as organic nitrates, glyceryl trinitrate, diazoxide, hydralazine, minoxidil, sodium nitroprusside, nicorandil, papaverine, alprostadil and calcium channel blockers such as amlodipine, nicardipine, nifedipine, verapamil, diltiazem, and nimodipine.

Angiotensin converting enzyme (ACE) inhibitors and angiotensin (AT) receptor antagonists such as captopril, enalapril are also used as well as α-adrenoceptor blocking drugs such as: prazosin, doxazosin, indoramin, phentolamine, dibenyline, thymoxamine, labetalol, ergot alkaloid, chlorpromazine.

β-Adrenoceptor blocking drugs such as oxprenolol, propranolol, pindolol, sotalol, timolol, nadolol, acebutolol, atenolol, bisoprolol, metoprolol, betaxolol, and labetalol are also useful for treating hypertension.

Other various therapies for treating hypertension include adrenergic neuron blocking drugs such as guanethidine, depletion of stored transmitter (noradrenaline) with reserpine, and inhibition of transmitter synthesis with metirosine.

Spasm of Alimentary Canal Smooth Muscle, Including Stomach, Intestine, Colons, Biliary and Pancreatic Duct Cholinergic receptor blockers or anticholinergic drugs such as atropine, hyoscyamine, hyoscine, hyoscine butylbromide, homatropine, tropicamine, ipratropium, flavoxate, oxybutynin, glycopyrronium, propantheline, dicyclomine, benzhexol, orphenadrine, promethazine, pirenzepine are currently used.

Spasm of Urinary Tract Smooth Muscle

Drugs similar to anticholinergic drugs mentioned above are being used.

Epilepsy

Epilepsy is a specific aspect of excessive contraction of skeletal muscle. For treating epilepsy, valproate, carbamazepine, phenyloin, lamotrigine, primidone, phenobarbital, gabapentin, vigabatrin, ethosuximide, clonazepam, felbamate, diazepam, among others are used.

Antiepileptic (anticonvulsant) drugs inhibit the neuronal discharge or its spread, and do so in one of the three ways:
  a) Altering cell membrane permeability to ions, e.g. $Na^+$, $Ca^{2+}$;
  b) Enhancing the activity of natural inhibitory neurotransmitters such as gamma-aminobutyric acid (GABA), which induces hyperpolarisation; and
  c) Inhibiting excitatory neurotransmitters, such as with glutamate.

For other skeletal muscle convulsion or spasm (such as Parkinson's disease, muscle spasm caused by various pathogenesis, including tetanus, some infectious diseases, some neurological diseases, and toxic spasm, such as poisoning of organophosphorus, and the like, phenobarbital, diazepam, magnesium sulfate are used.

Obviously, the effects of the medications, drugs, and therapies listed above on abnormal increased muscle tone or excessive muscle contraction are all aimed just at the pre-muscle molecular motor mechanism, i.e. initiating and regulating mechanisms, whereas the muscle molecular motor mechanism is set aside untargeted.

When the molecular motor enters in function, beginning with activation of actin-myosin ATPase, which catalyzes hydrolysis of ATP, and releases bio-energy for movement of the muscle molecular motor, the abnormal increased muscle tone or excessive muscle contraction may be effectively modified or attenuated by inhibition of the ATPase, regardless of the kind of muscle tissues, or their numerous differences in their pre-muscle molecular motor mechanisms, i.e. the initiating and regulating mechanisms. Therefore, the ATPase inhibitors may be used as bio-energy muscle relaxants (general muscle relaxants) for treating abnormal increased muscle tone or excessive muscle contractions of any kind of muscle tissues of human and animals under diseased conditions.

The Bio-Energy Muscle Relaxants (Also Referred to Herein as General Muscle Relaxants)

BDM (2,3-butanedione monoxime), also known as diacetyl monoxime, is a diffusible, non-toxic, and nucleophilic agent, which may dephosphorylate and reactivate acetylcholinesterase poisoned with organophosphorus. This chemical phosphatase activity stimulated studies of the effect of BDM on phosphorylation-dependent cellular processes. As a result of these studies, we know that the drug affects a number of mechanisms, including muscle contraction, ionic current flow and synaptic transmission. Furthermore, it may be used as a component of cardioplegic solutions since it protects cardiac muscle tissues exposed to certain ischaemic conditions. Meanwhile, diversity of its cellular actions is also being revealed resolving questions regarding its molecular mechanism. BDM is currently being used as a non-specific actin-myosin ATPase inhibitor or actin-myosin cross-bridge blocker in studies related muscle contraction.

BDM, also known as diacetyl monoxime, is a nucleophilic agent, which dephosphrylates acetylcholinesterase poisoned with organophosphates. This "chemical phosphates" activity stimulated studies of the effect of BDM on phosphorylation-dependent cellular processes. As result of these studies, we know that the drug affects a number of mechanisms including muscle contraction, ionic current flow and synaptic transmission. Furthermore, it may be used as a component of cardioplegic solutions since it protects cardiac tissues exposed to certain ischaemic conditions.

BDM has a cholinesterase reactivation activity. It may be rapidly absorbed with half-life of 0.09 to 0.12 h, peak blood concentration of 24.7±0.3 and 38.9±1.7 µg·ml−1 at 10 min. after 20–50 mg/kg, I.M. respectively. Eliminated half-life varied between 3.65±0.12 and 3.8±0.19 h.

Numerous in vitro and in vivo studies on animals have demonstrated that abnormal increased muscle tone or excessive muscle contraction, such as in asthma, hypertension, coronary malfunction, spasms of gastro-intestine tract, as well as skeletal muscle convulsion, may be substantially modified and attenuated when the muscle actin-myosin ATPase is inhibited by BDM. Therefore, the actin-myosin ATPase inhibitors, BDM and its isoforms, analogues, and other similar chemicals, possessing the inhibition effect on the actin-myosin ATPase, may be used as therapeutic agents for treating abnormal increased muscle tone or excessive muscle contraction in related diseases. The actin-myosin ATPase inhibitors is also referred herein as bio-energy muscle relaxants because they modify or attenuate abnormal increased muscle tone or excessive muscle contraction through inhibition of the actin-myosin ATPase, so as to reduce hydrolysis of ATP and then bio-energy release and consumption of the muscle tissues as well.

Controlling abnormal increased muscle tone or excessive muscle contraction in this way would completely differ from any of the current medications, drugs, and therapies adopted by doctors for these related diseases or symptoms.

The present invention will be more readily understood by referring to the following examples, which are given to illustrate the invention rather than to limit its scope.

EXAMPLE 1

Treatment of Asthma

Asthma is a common disease in adults and children, characterized by an increased smooth muscle tone or excessive contraction of bronchial smooth muscle in respond to atopic antigen exposures, and/or some other non-specific stimulation. Atopic allergy, bronchial hyperresponsiveness, and the subsequent series of pathophysiological alterations may be involved in the mechanisms of asthma. In fact, these mechanisms are falling into the aspect of pre-muscle molecular motor mechanism for asthmatic bronchial smooth muscle contraction.

Various medications and therapies such as with $\beta_2$-agonists, glucocorticoids, methylxanthines (for example theophylline), non-steroidal anti-inflammatory agents (for example cromolyn sodium and nedocromil sodium), leukotriene synthesis inhibitors, leukotriene receptor antagonists, lipoxygenase inhibitors and others.

All of these current medications or therapies for asthma are aimed just at the "pre-muscle molecular motor mechanism", i.e. the initiating and regulating mechanism of bronchial smooth muscle, including pathogenic causes and their following pathophysiological processes of asthma, whereas put the muscle molecular motor mechanism, i.e. contractile apparatus mechanism for bronchial smooth muscle aside and actually being ignored.

The inventors have demonstrated that BDM, an actin-myosin ATPase inhibitor, may induce a reversible bronchial smooth muscle relaxation. Therefore, BDM may be used as an airway smooth muscle relaxant (bronchodilator).

To investigate the bronchodilator effect of BDM, 15 guinea pigs of less than 200 g were used for the study. Sensitive animals were chosen by aerosolized inhalation of asthma-inducing agents—a mixed solution of 2% acetylcholine with 0.1% histamine for 15 sec., inducing an asthmatic attack with severe difficulty in respiration and finally resulting in the animal body turned down. The time from beginning of the inhalation to animal turned down was recorded as an index named "turned down time" or asthmatic latent period. Those animals with turned down time less than 120 s. were selected for the study next day. The selected animals were grouped and administered with saline (10 ml/kg, I.P.), BDM (0.2M, 10 ml/kg, I.P., purchased from Aldrich Company, and used without further purification, m.p., 76.8° C. HNMR, VAR 72, 2.0, 2.4, 8.9 in CDCl3; MS: 43 (100), 42 (20), 15 (11), 40 (9), 101 (7), 41 (7), 58 (4), 39 (4), 30 (4), 27 (4); IR: 3230, 3030, 2860, 1720, 1430, 1370, 1320, 1120, 1010, 980, 94, 790, 770), and aminophylline (1.25%, 10 ml/kg, I.P.) respectively at 30 min., 4 h, and 24 h. before inhalation of the asthma-inducing agent solution. Then the latent period was recorded for each of the animals.

Healthy guinea pigs with body weight <200 g, half male and female, were used to investigate effect of BDM on drug-induced asthma in guinea pig (mainly referring bronchodilator-like effect).

Experimental reagents and instruments: 0.2M BDM solution, 2% acetylcholine chloride, 0.1% histamine phosphate, 1.25% aminophyline, and type-402 ultrasonic nebulizer, etc.

Method (1) Screening animals: animal was put in a glass container, a mixed solution of 2% acetylcholine and 0.1% histamine was nebulized with a pressure of 400 mmHg and inhaled by the animals for 15 sec. Following the end of the inhalation, the time between beginning of the inhalation and the animal turned down due to bronchial spasm and dyspnea was recorded as asthmatic latent period. Those animals with a latent period beyond 120 s. were excluded, and those with a latent period less than 120 s were selected for study the next day.

(2) Grouping: The selected animals were divided into saline, BDM, and aminophyline groups.

(3) Administration of the drugs: saline (10 ml/kg, I.P.), BDM (0.2M, 10 ml/kg, I.P.) and aminophylline (1.25%, 10 ml/kg, I.P.) were given respectively before the inhalation.

(4) Measuring: Repeat the inhalation at 30 min, 4 h, and 24 h after administration of the drugs respectively. Asthmatic latent period was recorded, 6 minutes were taken as the maximum, and values beyond 6 min were counted as 6 min.

(5) Data analysis: Values were expressed as mean±sd, and paired for "t" and chi-square tests. Significance was considered to be established when $p<0.05$.

Results

Table 1 illustrates the effect of BDM on the asthmatic latent period induced by acetylcholine and histamine.

Conclusion

1) Thirty minutes after BDM given, the latent period was significantly extended compared to the value before BDM ($p<0.05$). The effect was similar with aminophylline.

2) Four and 24 h after SPL-A, found no significant effect on the latent period.

3) Thirty minutes and 4 h after aminophylline administration, the latent period was significantly extended ($p<0.05$).

4) Incidence of asthmatic spasm induced by the drugs at 30 min. after administration of BDM and aminophylline, showed a tendency to decrease, from 100% down to 60% and 40% respectively. (not reached significant level may be due to smaller sample size).

The results showed that 30 minutes after BDM administration, the asthmatic latent period induced by the asthma-inducing solution was significantly extended up to 261±107.4 s. (n=5) from 112±27.3 s. (n=5) for saline treated control group (P<0.05), and similar to the effect of aminophylline on bronchial smooth muscle.

EXAMPLE 2

Treatment of Abnormal Contraction of Bronchial Smooth Muscle

To investigate effect of BDM on abnormal contraction of bronchial smooth muscle induced by histamine, 15 guinea pigs with body weight of 250~350 g were used for the study.

TABLE 1

| | | | Asthamatic Latent Period (s) | | | |
|---|---|---|---|---|---|---|
| | Dose | Body Wt | Before | After administration | | |
| Group | (ml/kg) | (g) | administration | 30 minutes | 4 hours | 24 hours |
| N.S. | 10 | 179.8 ± 16.7 (n = 5) | 91.8 ± 17.3 (n = 5) | 112.0 ± 27.3 (n = 5) | 91.0 ± 40.1 (n = 5) | 111.8 ± 59.7 (n = 5) |
| BDM | 10 | 179.3 ± 14.5 (n = 5) | 70.4 ± 21.1 (n = 5) | 261.0 ± 107.4 (n = 5) ▲# | 99.2 ± 42.1 (n = 5) Δ | 81.8 ± 11.0 (n = 5) |
| Aminophylline | 10 | 179.3 ± 20.8 (n = 5) | 70.6 ± 27.7 (n = 5) | 298.2 ± 138.2 (n = 5) ▲## | 216.6 ± 112.5 (n = 5) ▲# | 96 ± 26.9 (n = 2) |

Notes:
*P < 0.05 BDM compared to saline;
P < 0.05,
P < 0.01 aminophylline compared to saline;
▲P < 0.05 BDM comapred to aminophylline;
ΔP < 0.05 compared before and after the administration.

Table 2 illustrates the effect of BDM on incidence of asthmatic spasm induced by acetylcholine & histamine.

TABLE 1

| | | | Asthamatic Latent Period (s) | | | |
|---|---|---|---|---|---|---|
| | Dose | Body Wt | Before | After administration | | |
| Group | (ml/kg) | (g) | administration | 30 minutes | 4 hours | 24 hours |
| N.S. | 10 | 179.8 ± 16.7 (n = 5) | 100 (n = 5) | 100 (n = 5) | 100 (n = 5) | 100 (n = 5) |
| BDM | 10 | 179.3 ± 14.5 (n = 5) | 100 (n = 5) | 100 (n = 5) | 100 (n = 5) | 100 (n = 5) |
| Aminophylline | 10 | 179.3 ± 20.8 (n = 5) | 100 (n = 5) | 100 (n = 5) | 100 (n = 5) | 100 (n = 2) |

The animals were divided as saline, BDM, and aminophylline groups. Each animal was anesthetized with pentobarbital (30 mg/kg, I.P.), the trachea was intubated and connected to respirator. Tidal volume and frequency of the respirator were adjusted to 6~10 ml and 60~70 breath/min. respectively.

A small hole on chest wall of the animal was made, resulting in pneumothorax to inhibit spontaneous respiration of the animal. A modified device was used for measuring by-pass-airflow pressure of the airway, reflecting alteration in airway resistance, therefore evaluating status of bronchial smooth muscle contraction induced by histamine. The by-pass-airflow pressures were measured before and at 10, 20, 30, 40, 50, and 60 min after administration of histamine (5~10 μg, I.P.) as control values. Then, saline (10 ml/kg, I.P.), BDM (0.2M, 10 ml/kg, I.P.), and aminophylline (1.25%, 10 ml/kg, I.P.) were given respectively, the by-pass-airflow pressures induced by the same dose histamine before and at the same time points after the administration of the drugs were recorded. Changes in by-pass-airflow pressure caused by histamine before and after saline, BDM, or aminophylline were compared.

A percentage of changes in the airflow pressures before and after administration of the histamine at different time points, defined as the change rate, was calculated according to formula 1 below:

$$\text{Change rate (\%)} = (PA-PB)/PB \times 100\% \quad (1)$$

where PA is the airflow pressure after histamine, PB is the pressure before histamine. Values were expressed as mean±SD, paired or group "t" test was used upon the requirement for the statistical analysis. The results were considered significant when p<0.05.

Experimental reagents and instruments: BDM (0.2 M), histamine phosphate (10 μg/ml), 1.25% aminophylline, saline, DH-140 animal respirator, and multiple-channel physiology recorder, etc.

Method (1). Group, dosage and administration: the animals were grouped as saline (10 ml/kg, I.P.), BDM (0.2 M, 10 ml/kg, I.P.) and 1.25% aminophylline (10 ml/kg, I.P.) (positive) groups.

Table 3 illustrates the effect of the tested drugs on by-pass-airflow pressure.

TABLE 3

| | Saline Group (Kpa) | | BDM Group (Kpa) | | Aminophylline (Kpa) | |
|---|---|---|---|---|---|---|
| | B | A | B | A | B | A |
| B. Hist | 3.84 ± 0.30 | 3.85 ± 0.30 | 3.60 ± 0.26 | 3.86 ± 0.23 | 4.18 ± 0.72 | 4.24 ± 1.18 |
| Hist 10 min. | 4.10 ± 0.29 | 3.94 ± 0.21 | 3.67 ± 0.16 | 3.42 ± 0.21 | 4.51 ± 0.65 | 4.36 ± 1.10 |
| Hist 20 min. | 4.04 ± 0.27 | 4.04 ± 0.37 | 3.76 ± 0.32 | 3.54 ± 0.21 | 4.34 ± 0.73 | 4.18 ± 0.86 |
| Hist 30 min. | 3.97 ± 0.36 | 3.98 ± 0.27 | 3.72 ± 0.21 | 3.56 ± 0.27 | 4.40 ± 0.79 | 4.20 ± 0.92 |
| Hist 40 min. | 3.94 ± 0.38 | 4.02 ± 0.23 | 3.72 ± 0.18 | 3.60 ± 0.28 | 4.42 ± 0.80 | 4.15 ± 0.88 |
| Hist 50 min. | 3.88 ± 0.24 | 3.98 ± 0.30 | 3.67 ± 0.23 | 3.62 ± 0.29 | 4.42 ± 0.86 | 4.10 ± 0.92 |
| Hist 60 min. | 3.94 ± 0.32 | 3.95 ± 0.37 | 3.68 ± 0.11 | 3.66 ± 0.26 | 4.46 ± 0.87 | 4.02 ± 0.92 |

Table 4 illustrates the effect of the tested drugs on changing rate of by-pass-airflow pressure.

TABLE 4

| | Saline Group (%) | | | BDM Group (%) | | | Aminophylline (%) | | |
|---|---|---|---|---|---|---|---|---|---|
| | B | A | D | B | A | D | B | A | D |
| Hist 10 min. | 6.94 ± 6.05 | 2.51 ± 3.57 | −4.43 ± 6.47 | 2.13 ± 3.72 | −11.37 ± 2.70▲▲ | −13.50 ± 3.25★ | 8.37 ± 7.65 | −7.68 ± 7.30▲ | −16.05 ± 11.76 |
| Hist 20 min. | 5.35 ± 4.53 | 5.05 ± 7.89 | −0.29 ± 4.59 | 4.49 ± 5.60 | −8.22 ± 3.78▲ | −12.72 ± 8.83★ | 3.93 ± 5.67 | −10.62 ± 9.93▲ | −14.55 ± 11.05 |
| Hist 30 min. | 3.38 ± 4.46 | 3.45 ± 1.90 | 0.06 ± 3.77 | 3.52 ± 5.09 | −7.80 ± 3.26▲ | −11.33 ± 6.86★ | 5.31 ± 7.95 | −10.40 ± 9.47▲ | −15.71 ± 11.78 |
| Hist 40 min. | 2.54 ± 3.98 | 4.59 ± 4.08 | 2.05 ± 5.17 | 3.56 ± 5.14 | −6.77 ± 3.58▲ | −10.34 ± 6.40★★ | 5.80 ± 9.09 | −11.38 ± 8.54▲ | −17.19 ± 13.20 |
| Hist 50 min. | 1.20 ± 4.12 | 3.48 ± 5.28 | 2.28 ± 2.54 | 2.06 ± 3.88 | −6.25 ± 3.92▲ | −8.31 ± 5.90★★ | 5.63 ± 9.46 | −12.73 ± 8.21▲ | −18.36 ± 10.52 |
| Hist 60 min. | 2.64 ± 3.78 | 2.51 ± 3.74 | −0.12 ± 3.87 | 2.54 ± 5.95 | −5.11 ± 5.64 | −7.65 ± 6.83 | 6.54 ± 8.83 | −14.25 ± 9.52▲ | −20.79 ± 13.84 |

Notes: ★P < 0.05, ★★P < 0.01 BDM compared to saline, #. P < 0.05, ## P < 0.01 saline compared to aminophylline, ▲P < 0.05, ▲▲P < 0.01 before and after the administration of the drugs.

Conclusion

1) Administration of the histamine caused significant increase in the airflow pressure, reflecting a raised bronchial smooth muscle tone due to smooth muscle contraction ($p<0.05$).

2) BDM may significantly reduce the histamine-induced increase in the airflow pressure at 10, 20, 30, 40, and 50 min after the administration of BDM ($p<0.01$, or $p<0.05$).

3) Aminophylline may significantly reduce the histamine-induced increase in the airflow pressure at 10, 20, 30, 40, 50, and 60 min after administration of aminophylline ($p<0.01$, or $p<0.05$).

4) Effect of BDM was similar to that of aminophylline at the time points after administration of the two tested drugs.

5) Both BDM and aminophylline possess relaxing effect on contracted bronchial smooth muscle.

The results showed that at 10', 20', 30', 40', and 50' after the administration of BDM, the histamine-airflow pressures were significantly deceased compared to the values before the administration of BDM ($P<0.01$ or $P<0.05$), suggesting BDM possesses significant relaxing effect on contraction of bronchial smooth muscle induced by histamine, whereas without reducing of normal bronchial smooth muscle tone, similar to the effect of aminophylline on bronchial smooth muscle.

EXAMPLE 3

Treatment of Abnormal Excessive Contractions of Smooth Muscle in Gastrointestinal, Biliary, Pancreatic, and Urinary Tracts Abnormal excessive contractions of smooth muscle in gastro-intestinal tract, biliary, pancreatic, and urinary tracts, are often shown as severe and emergent symptoms. They are usually caused by numerous pathogenetic factors, such as acute inflammatory processes, stimulation of stones or parasites in these organs. Anticholinergic drugs are currently used for relief of the abnormal excessive contraction of smooth muscle in these organs, such as atropine, scopolamine, anisodamine, and synthesized anticholinergic drugs, often combined with sedatives and analgesics, even morphine.

All these drugs used for relief of smooth muscle spasm in alimentary tract, acting at the peripheral terminals of autonomic nervous system in these organs, blocking or reducing release of cholinergic neurotransmitters, so as to modify or attenuate abnormal contraction of smooth muscle in these organs. The mechanism falls in the aspect of the pre-muscle molecular motor mechanisms, i.e. the initiating and regulating mechanisms, but put the molecular motor mechanisms aside without directly intending to effect on it.

It is demonstrated in accordance with the present invention that, BDM possesses significant inhibition of abnormal smooth muscle contraction induced by BaCl2 in isolated colon tissues from guinea pigs.

To investigate this effect, 14 guinea pigs (provided by the Center of Experimental Animals, First Military Medical University, Guangzhou, China, certificate No. 99A047) with body weight of 240±20 g were used for the study. Following sacrifice of the animal by cervical dislocation, the colon was isolated within Botting solution, a segment of the colon in 2 cm length was taken to mount on the equipment—one end connected to a force transducer, the other end fixed at the bottom of the organ water-bath (DC-001 Organ Bath, made in Nanjin, China) containing oxygenated nutritious solution at 37° C. The force (g) resulted from smooth muscle contraction caused by $BaCl_2$ (AR, product of Guangzhou Chemical Reagent Factory, Lot. No. 20000301-2) (0.67 g/L nutritious sol.) was measured before and 10 min. after the administration of placebo (nutritious sol.) or BDM (0.2M, 20 ml/L nutritious sol.). A contraction rate after the administration of placebo and BDM was calculated according to formula 2 below:

$$\text{Contraction Rate} = \frac{\text{Contraction force after } BDM \text{ (or placebo)}}{\text{Contraction force before } BDM \text{ (or placebo)}} \times 100\% \qquad (2)$$

Group "t" test was then made. Significance is considered to be established when $P<0.05$ The result showed that BDM (20 ml/L nutritious solution) possesses significant inhibition of isolated colon smooth muscle contraction induced by $BaCl_2$.

Materials

Experimental Reagents: BDM (0.2M, pink solution), provided by Jia-Jie-Xing Science & Technology Co., Shengzheng, China, Lot. 20000720

Main Reagents

Smooth muscle stimulator: barium chloride ($BaCl_2$) A.R, product of Guangzhou Chemical Reagent Factory Lot. No. 20000301-2.

Instrument

Type DC-001 Organ Bath, Nanjing Analytical Instruments Co., China.

The animals were divided as test group and control (placebo) group. $BaCl_2$ (0.67 g/L. nutritious solution) was added into the water bath to induce smooth muscle contraction of the colon before administration of BDM or distilled water, repeating the same procedures and measuring the contraction force for times until a stable amplitude of the contraction reached. Following times of washing then, BDM (0.2M, 20 ml/L nutritious sol.) or same amount of distilled water was added separately, 10 min afterwards, same dose of $BaCl_2$ was added into the water bath again, to observe effect of BDM or distilled water on the colon smooth muscle contraction induced by BaCl2. The contraction force before and after administration of BDM or distilled water was recorded, and a contraction rate was calculated according to formula 3 below:

$$\text{Contraction Rate } (\%) = \frac{(Fc \text{ after the drug})}{(Fc \text{ before the drug})} \times 100\% \qquad (3)$$

Where Fc is force of the smooth muscle contraction.

Paired group "t" test was made to compare contraction force after BDM and distilled water to determine whether there is a significant difference between the two groups. The result was listed as below:

| Control | | | | | | | |
|---|---|---|---|---|---|---|---|
| Before (g) | 2.05 | 2.70 | 1.95 | 3.10 | 1.70 | 2.60 | 2.40 |
| After (g) | 2.00 | 2.85 | 2.00 | 3.10 | 1.65 | 2.80 | 2.35 |
| Rate (%) | 97.5 | 105.5 | 102.6 | 100.0 | 97.1 | 107.7 | 97.9 |
| Mean ± SD: 101.2 ± 4.2% | | | | | | | |

-continued

Test

| | | | | | | | |
|---|---|---|---|---|---|---|---|
| Before (g) | 2.35 | 2.30 | 2.35 | 2.30 | 2.45 | 2.70 | 2.90 |
| After (g) | 1.70 | 1.35 | 1.45 | 1.75 | 1.70 | 1.75 | 2.20 |
| Rate (%) | 72.3 | 58.7 | 61.7 | 76.1 | 69.4 | 64.8 | 75.9 |

Mean ± SD: 68.4 ± 6.9%

The result showed that the contraction rate after administration of BDM was 68.4±6.9%, significantly lower than 101.2±4.2%, that of control group (P<0.01). It suggests that BDM possesses significant relaxing effect on abnormal colon smooth muscle contraction caused by BaCl2 in guinea pigs.

EXAMPLE 4

Treatment of Hypertension

Hypertension is a disease mainly related to abnormal increased muscle tone or excessive contraction of systemic arterial smooth muscle. The pathogenetic mechanism for hypertension is very complicated. However, it's recognized that an increased arterial smooth muscle tone certainly plays a very important role in the disease. Although numerous medications, drugs, and therapies have been developed for treating hypertension, including reducing arterial smooth muscle tone, all of them, however, effect just on the events involved in aspect of the pre-muscle molecular motor mechanism, i.e. the initiating and regulating mechanism, but without directly intending to effect on the molecular motor mechanism of arterial smooth muscle, which basically is the same as other smooth muscles.

The physiological control and regulation of blood pressure involve many extreme complicated processes, including neurogenic and humoral mechanisms. Among them, sympathetic (adrenergic nervous) system and renin-angiotensin-aldosterone system play significant influence with blood pressure. In fact, lots of anti-hypertension drugs are acting through modulating of these two systems, relaxing arterial smooth muscle or reducing blood volume, so as to lower blood pressure.

According to the sites on which drugs influence, anti-hypertension drugs may be classified as the following:
  i) Drugs that mainly affect the centers of the adrenergic nervous system, such as Clonidine, α-Methyldopa, and so on, =2-receptor agonists. The drug may bind with α2-receptors on neuron posterior-membrane at central nervous system, so as to stimulate the inhibitory neurons, resulting in inhibition of peripheral sympathetic activities. In addition, α2-receptor on prior-membrane of the peripheral sympathetic neuron may also be stimulated, reducing release of noradrenaline from the sympathetic terminals.
  2. Ganglia blockers such as Hexamethonium. These drugs are antagonists of $N_1$-cholinergic receptor on neurons in ganglia, so, they may block neuro-transmission at ganglia. Blocking of sympathetic ganglia results in tremendous decrease in blood pressure. Meanwhile, parasympathetic ganglia may also be blocked, causing many side effects. Therefore, these kinds of drugs actually are seldom used in medical practice.
  3. Peripheral anti-noradrenergic drugs, such as Reserpine, and guanethidine. These drugs may block the intake process of amines and result in depletion of the neurotransmitters.
  4. Adrenergic Blockers such as α-receptor blockers (for example Prazosin), Preceptor blockers (for example punelol, medolol, nadolol), and Blockers for both α- and β-receptors (for example Labetolol).
  5. Drugs affecting on vasculature smooth muscle such as Hydralazine, Diazoxide, Minoxidil, Sodium Nitroprusside.
  6. Blockers of $Ca^{2+}$ channel such as Nifedipine, and Tetrandrine.
  7. Drugs that mainly affect blood volume-Diuretics Hydrochlorothiazide.
  8. Angiotensin I converting Enzyme Inhibitors (ACEI) such as Captopril, Enalapril, and Ramipril.

In accordance with the present invention, it is demonstrated in in vivo studies on rats (reported herein) that, BDM may efficiently antagonize hypertension induced by aramine, and apparently inhibit the increased blood pressure in the rat hypertension model.

Eighteen (18) SD rats (provided by the Center of Experimental Animals, First Military Medical University, Guang Zhou, China, Certificate No. 99A046) with body weight of 200–250 g were used for the study. The animal was anesthetized with urethane (1.4 g/kg, I.P.), then the main cervical artery was exposed and cannulated, blood pressure was monitored during the experiment. After a 30-minute stabilization period after the operation, normal blood pressure curves were recorded.

Preventive Test

BDM (0.2 M, 10 ml/kg, I.P.) or the same amount of saline as control was given first, then blood pressure curves at 2, 5, 10 min. after the administration were recorded respectively, and followed by administration of aramine (30 μg/ml, 0.4 ml/min, I.V. drop) through femoral vein, blood pressure curves were recorded at 2, 5, 10 min. after the administration of aramine.

Curative Test

The same amount of aramine was given first, inducing blood pressure to increase by about 60 mmHg, stabilized for 10 min., then BDM (0.2 M, 10 ml/kg, I.P.) or saline as control was administered, blood pressure curves were recorded at 2, 5, 10 min after BDM or saline.

Table 5 illustrates the effect of BDM on hypertension caused by aramine in the rats (mmHg, mean±SD, n=6–7).

TABLE 5

| | | Blood pressure after BDM administration | | | Blood Pressure after aramine administration | | |
|---|---|---|---|---|---|---|---|
| | Blood Pressure before | 2 minutes | 5 minutes | 10 minutes | 2 minutes | 5 minutes | 10 minutes |
| Control S. | 120.0 ± 13.8 | 115.6 ± 13.9 | 117.3 ± 8.4 | 124.1 ± 8.9 | 184.4 ± 8.5 | 179.9 ± 6.9 | 184.0 ± 11.8 |

TABLE 5-continued

| | Blood pressure after BDM administration | | | Blood Pressure after aramine administration | | |
|---|---|---|---|---|---|---|
| Blood Pressure before | 2 minutes | 5 minutes | 10 minutes | 2 minutes | 5 minutes | 10 minutes |
| Control D. 70.0 ± 8.5 | 65.4 ± 8.8 | 68.0 ± 4.8 | 70.7 ± 10.6 | 115.7 ± 11.3 | 116.0 ± 6.2 | 117.4 ± 9.8 |
| Priven. S. 117.3 ± 3.2 | 88.0 ± 5.2** | 84.0 ± 6.7** | 88.2 ± 7.7** | 126.3 ± 16.1** | 127.5 ± 16.1** | 127.7 ± 17.3** |
| Priven. D. 68.7 ± 8.8 | 39.7 ± 6.4** | 39.0 ± 8.7** | 43.0 ± 8.5** | 76.2 ± 21.5** | 76.5 ± 11.9** | 77.0 ± 22.4** |

Notes: S means systolic pressure (SBP), D means diastolic pressure (DBP). *P < 0.05, **P < 0.01 when compared to the control.

Table 6 illustrates the effect of BDM on hypertension—caused by aramine in the rats (mmHg, mean±SD, n=6–7)

TABLE 6

| | Blood pressure after aramin administration | | | Blood Pressure after BDM administration | | |
|---|---|---|---|---|---|---|
| Blood Pressure before | 2 min. | 5 min. | 10 min. | 2 min. | 5 min. | 10 min. |
| Control S. 127.7 ± 12.8 | 185.9 ± 9.0 | 182.9 ± 10.6 | 186.3 ± 13.4 | 186.7 ± 11.7 | 186.7 ± 9.8 | 191.6 ± 14.7 |
| Control D. 77.9 ± 22.8 | 123.7 ± 21.1 | 125.3 ± 21.5 | 126.1 ± 21.5 | 125.6 ± 19.5 | 129.0 ± 19.7 | 130.7 ± 22.9 |
| Priven. S. 123.3 ± 10.1 | 182.7 ± 6.0 | 183.5 ± 5.5 | 181.8 ± 6.4 | 123.7 ± 6.0** | 128.3 ± 5.2** | 130.5 ± 4.2** |
| Priven. D. 74.0 ± 15.4 | 121.5 ± 5.5 | 122.2 ± 5.1 | 117.7 ± 9.5 | 73.8 ± 4.9** | 77.0 ± 9.1** | 76.3 ± 5.2** |

Notes: S means systolic pressure (SBP), D means diastolic pressure (DBP), *P < 0.05, **P < 0.01 when compared to the control.

The results showed that: (1) In the preventive test, the blood pressure was apparently decreased after administration of BDM, from 117/68 down to 84/40 mmHg approximately. Following aramine administration then, the blood pressure in BDM group was recovered and maintained at normal level, at about 125/75 mmHg, whereas values of the blood pressure in control group were obviously higher than normal, at about 185/120 mmHg. (2) In the curative test, the blood pressure was significantly decreased, averaged by 54/42 mmHg, after BDM administration, in contrast to the blood pressure in control group that was just fluctuating within a range of ±15 mmHg. It suggests that BDM may decrease smooth muscle tone of the arterials, may also effectively antagonize aramine-induced hypertension, and possesses significant inhibition of hypertension activity. Therefore actin-myosin ATPase inhibitor, BDM, may be used as an effective treatment for hypertension that mainly due to an abnormally increased arterial smooth muscle tone.

EXAMPLE 5

Treatment of Abnormal Contraction of Skeletal Muscle

Abnormal contraction of skeletal muscle, such as epilepsy, some infectious diseases, some neurological diseases, toxic spasm, tetanus, poisoning of organophosphurus, is very common in clinic emergency medicine. The anticonvulsants currently used for these skeletal muscle convulsions are all effective just on the mechanisms before muscle molecular motor, i.e. the initiating and regulating mechanisms, without directly intending to effect on the muscle molecular motor mechanism, recycling of the actin-myosin filament cross-bridge and sliding movement.

To investigate the effect, 36 mice (provided by the Center of Experimental Animals, Provincial Health Department, Guangdong, China, Certificate No. 99A030) were used for the study, the animals were grouped as placebo, preventing, and treatment groups. Muscle convulsion was induced with injection of strychnine (1.5 mg/kg I.P., injection product of 2 mg/ml, He Feng Pharmaceutical Co., Shanghai, China, Lot. No. 990701), the beginning and lasting time of the convulsion were recorded. Then the same experimental procedure was repeated and the convulsion were measured before and after administration of BDM (0.2M, 20 ml/kg, I.P.) or saline to determine if the convulsion induced by strychnine were modified.

Half male and female healthy NIH mice with body weight of 20±2 g were selected for the study. The animals were randomly divided into three groups as protective, curative, and control (saline). For the protective group, BDM (0.2M, 20 ml/kg, I.P.) was given 0.5 h prior to administration of strychnine (1.5 mg/kg, I.P.). For the curative group, then the same dose of BDM was given immediately after strychnine administration. In the control group, saline (20 ml/kg, I.P.) was administered 0.5 h before the strychnine. Immediately following the injection of strychnine, convulsion latent period and the time from beginning of convulsion to death of the animal were recorded. The animals showed reducing activities, difficulties in action and toddling after administration of BDM. Two or three min. following the strychnine administration, the animals showed suddenly turning to exciting, running around, and finally leading to rigidly convulsion. (see Table 7).

TABLE 7

Antagonistic effect of BDM on convulsion caused by
the lethal dose of strychnine (mean ± SD, n = 12)

| Groups time | Convulsion (%) | Death (%) | The latent period (s) | Convulsion-Death (s) |
|---|---|---|---|---|
| Control | 100 | 100 | 218.3 ± 39.4 | 10.8 ± 20.9 |
| BDM curative | 100 | 100 | 134.2 ± 31.5 | 538.3 ± 169.3** |
| BDM preventive | 100 | 100 | 183.8 ± 32.6 | 496.3 ± 285.3** |

Notes: **P < 0.01 when compared to control.

The results showed that BDM may significantly extend the time from beginning of convulsion to the death of the animal (P<0.01), the values were 496.3±285.3 s., 538.3±169.3 s. and 10.8±20.9 s. in preventive, curative and saline group respectively, suggesting BDM possesses antagonist effect against the convulsion induced by strychnine, so that BDM may potentially be used as an anticonvulsant.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method for treating and/or preventing a smooth muscle contraction related disease or condition, said method comprising conventionally administering by inhalation, orally, topically, parenterally, on mucous or skin tissues, subcutaneously, intramuscularly, intravenously, intraperitoneally or by topical tissue infiltration injection to a patient in need thereof a muscle relaxant as defined in formula II:

$$R_1C(=NOH)COR_2 \quad (II)$$

where $R_1$ and $R_2$, identical or different, are each selected from the group consisting of $C_{1-8}$ linear or branched alkyl and cycloalkyl with the proviso that $R_1$ and $R_2$ are not both methyl group and that when $R_1$ is a methyl group, $R_2$ is not an ethyl or propyl group.

2. The method of claim 1, wherein $R_1$ and $R_2$ are independently selected from the group consisting of methyl, ethyl and propyl.

3. The method of claim 1, wherein the muscle contraction-related disease is selected from the group consisting of asthma, spasm of trachea-bronchial tree smooth muscle, diaphragm muscle abnormal contraction, breathlessness, dyspnea, diaphragmatic convulsion, hypertension, abnormal contraction of bronchial smooth muscle, abnormal and/or excessive contraction of smooth muscle in systemic, coronary and pulmonary circulation, and micro-circulatory smooth muscle, systemic hypertension, malignant hypertension, hypertension crisis, symptomatic hypertension, pulmonary hypertension, pulmonary infarction, angina pectoris, infarction, cardiac infarction, and micro-circulation malfunction under shock condition.

4. The method of claim 1, wherein said smooth muscle contraction related disease is asthma.

5. The method of claim 1, wherein said smooth muscle contraction related condition is abnormal contraction of bronchial smooth muscle.

6. The method of claim 1, wherein said smooth muscle contraction disease or condition is concerned with the gastrointestinal tract, the biliary tract, the pancreatic tract, or the urinary tract.

7. The method of claim 1, wherein said smooth muscle contraction condition is hypertension.

8. The method of claim 4, wherein said muscle relaxant is conventionally administered by inhalation.

9. The method of claim 1, wherein said muscle relaxant is administered to a patient to obtain a concentration of about 2 mM/L muscle relaxant in the tissue.

* * * * *